United States Patent [19]

Verite et al.

[11] Patent Number: 4,980,078

[45] Date of Patent: Dec. 25, 1990

[54] TRANSPARENT SOAP COMPOSITION BASED ON SOAPS OF TALLOW FATTY ACIDS AND WATER AND ON AT LEAST ONE 1,2-ALKANEDIOL

[75] Inventors: Claude Verite, Paris; Alain Caudet, Boulogne Billancourt, both of France

[73] Assignee: L'Oreal, Paris, France

[21] Appl. No.: 326,923

[22] Filed: Mar. 22, 1989

[30] Foreign Application Priority Data

Mar. 24, 1988 [LU] Luxembourg .............................. 87179

[51] Int. Cl.$^5$ ......................... C11D 17/00; C11D 9/26
[52] U.S. Cl. .................................... 252/118; 252/108; 252/121; 252/132; 252/134; 252/DIG. 16
[58] Field of Search ............... 252/108, 118, 132, 134, 252/DIG. 16

[56] References Cited

U.S. PATENT DOCUMENTS

| | | |
|---|---|---|
| 3,562,167 | 2/1971 | Kamen et al. ......................... 252/121 |
| 3,793,214 | 2/1974 | O'Neill et al. ....................... 252/117 |
| 4,165,293 | 8/1979 | Gordon ................................. 252/118 |
| 4,206,069 | 6/1980 | Borrello ............................... 252/122 |
| 4,290,904 | 9/1981 | Poper et al. .......................... 252/118 |

FOREIGN PATENT DOCUMENTS 527258 7/1956 Canada .
2669986 5/1986 Japan .
1300415 12/1972 United Kingdom .

Primary Examiner—Prince E. Willis
Attorney, Agent, or Firm—Marshall, O'Toole, Gerstein, Murray & Bicknell

[57] ABSTRACT

Composition in the form of a transparent, solid cake containing a soap consisting of a salt of $C_{10}$–$C_{20}$ fatty acids, a 1,2-alkanediol containing from 10 to 18 carbon atoms, a transparency agent, and water in quantities of less than or equal to 25% by weight relative to the total weight of the composition.

15 Claims, No Drawings

TRANSPARENT SOAP COMPOSITION BASED ON SOAPS OF TALLOW FATTY ACIDS AND WATER AND ON AT LEAST ONE 1,2-ALKANEDIOL

The present invention relates to a transparent, solid soap composition based on soaps of tallow fatty acids comprising at least one 1,2-alkanediol.

Transparent, solid soap compositions are well-known in the state of the art. They generally consist, with or without alcohol, of soaps of tallow and/or copra and/or castor fatty acids and of transparency agents, preferably chosen from polyols such as the sugars and glycerine or glycols such as propylene glycol, ethylene glycol or mixtures of these last-mentioned.

In the case of alcohol-free solid soaps, a soap content of less than 40% and especially less than 20% of soaps of copra fatty acids is generally employed to improve their transparency.

These compositions, which are known in the cosmetics field, exhibit the disadvantage of producing little foam. Attempts have been made to improve their foaming power by the addition of synthetic anionic surface-active agents such as alkali metal olefin-sulphonates.

Alcohol-free solid soap compositions of the same type are also known, also containing a synergistic foaming agent such as copra diethanolamide.

Applicants have surprisingly found that on introducing a 1,2-alkanediol into a transparent solid soap composition, alcohol-free, based on soaps of fatty acids, the foam qualities of the composition were appreciably improved, in particular its abundance, its texture, its softness and its speed of development.

The compositions according to the invention exhibit foam qualities which are superior to those obtained with the copra diethanolamide employed previously and conventionally, or when compared with another synergistic foam agent such as the (copra)-alkylamidopropyl-dimethylglycine sold under the name "Tego Betain L7" by Goldschmidt.

The subject matter of the present invention is therefore a detergent and foaming cosmetic composition existing in the form of transparent, solid soap based on soaps of tallow fatty acids, water and transparency agents and containing at least one 1,2-alkanediol.

Another subject of the invention is a washing process making use of the composition defined above.

Further subjects of the invention will become apparent from reading the description and the examples which follow.

The composition in accordance with the invention is in the form of a transparent, solid cake and is essentially characterized by the fact that it contains a soap consisting of salts of $C_{10}-C_{20}$ fatty acids, a 1,2-alkanediol, a transparency agent and water in quantities of less than or equal to 25% of the total weight of the composition.

The 1,2-alkanediols which can be employed in the present invention are saturated compounds containing a linear chain with an even or odd number of carbon atoms capable of containing from 10 to 18 and preferably from 10 to 14 carbon atoms. 1,2-Dodecanediol is the preferred 1,2-alkanediol. They may be conveniently obtained by hydroxylation of α-olefins or hydrolysis of the corresponding epoxides.

The 1,2-alkanediol is preferably employed in weight proportions of between 3 and 10%, preferably between 4 and 8% and still more particularly between 5 and 7% relative to the total weight of the composition.

The soaps employed according to the invention are preferably chosen from sodium salts, in particular from sodium salts of $C_{16}-C_{20}$ fatty acids and the sodium salts of $C_{10}-C_{14}$ fatty acids or a mixture thereof. They are preferably employed in proportions of between 25 and 40%, in particular between 25 and 35% relative to the total weight of the composition. Particularly advantageous results are obtained in the case of proportions of between 27 and 32% by weight.

A preferred embodiment of the invention consists in employing a soap containing a quantity of sodium salts of $C_{16}-C_{20}$ fatty acids of between 80 and 90% by weight and a quantity of sodium salts of $C_{10}-C_{14}$ fatty acids between 10 and 20% by weight.

The transparency agents, which are also solvent, are chosen from $C_2-C_6$ polyols such as, more particularly, glycerine, propylene glycol and sorbitol or, optionally, urea and mixtures of these.

They are preferably employed in proportions of between 25 and 50%.

A preferred transparent, solid soap composition consists of a cake comprising:

(i) 25 to 40% of a soap consisting of a mixture of sodium salts of $C_{16}-C_{20}$ fatty acids and of sodium salts of $C_{10}-C_{14}$ fatty acids;

(ii) 3 to 10% of 1,2-dodecanediol;

(iii) 25 to 50% of a $C_2-C_6$ polyol or of urea;

(iv) water in proportions of less than or equal to 25% by weight.

The presence of 1,2-alkanediol in the transparent, solid soap compositions according to the invention considerably modifies, by means of a synergistic effect, their foaming properties and the appearance of the foam resulting therefrom.

The findings are, in fact: a very marked improvement in starting to foam, a great increase in the foaming power, and an improvement in the appearance of the foam, which is thicker, has better consistency and is more unctuous and therefore pleasanter to the touch; foam stability is also increased.

In addition to its detergent and foaming properties, the soap employed in accordance with the present invention has the advantage of being non-irritant to the skin.

The solid and transparent soap compositions defined above may additionally contain a synthetic anionic or nonionic surface-active agent chosen from sodium ($C_{14}-C_{16}$)-olefinsulphonate, triethanolamine laurylsulphate, sodium N-lauroylsarcosinate sold under the names "Sarkosyl NL 30" by Ciba Geigy or "Oramix L 30" sold by Seppic, the potassium salt of a condensate of copra fatty acids and of a hydrolysed animal protein, sold under the name "Lamepon S" by Grunau, an ether of glucose and of decyl alcohol sold at 50% of active substance (AS) under the name "Triton CG 312" by Seppic, or an alkali metal (linear or branched $C_9-C_{18}$)-alkyl ether sulphate comprising 1 to 10 moles of ethylene oxide, such as a sodium (linear $C_{12}-C_{14}$)-alkyl ether sulphate containing approximately 2.2 moles of ethylene oxide, or a sodium (branched $C_{13}-C_{15}$)-alkyl ether sulphate containing 3 moles of ethylene oxide, sold by ICI under the name Tensagex DLM 970.

When present, these anionic or nonionic surface-active agents are employed in the compositions according to the invention in proportions of between 1 and 10% and preferably between 4 and 8% relative to the total weight of the composition.

They may also contain sequestering or chelating agents, such as tetrasodium ethylenediaminetetraacetate and tetrasodium 1-hydroxy-ethylidenediphosphonate. They are employed in proportions of 0.1 to 0.5% by weight relative to the total weight of the composition.

The transparent, solid soap compositions according to the invention may also contain adjuvants which do not modify their transparency, such as pearlescent agents and nonvolatile silicones, in a weight proportion of less than 5%, and skin conditioning agents such as polymers, aloe or mallow extracts, sunflower oil or collagen in a weight proportion of less than 2%. The compositions in accordance with the invention may also contain active ingredients for skin treatment, such as antiacne agents and antibacterial agents; they may also contain colorants and other adjuvants usually employed in cosmetics.

Another subject of the invention is a process for washing the skin, characterized in that a transparent solid soap such as defined above is applied to moist skin.

The following examples illustrate the invention without, however, limiting it.

EXAMPLE 1

A transparent, solid soap of the following composition is prepared:

| | |
|---|---|
| Stearic acid | 22 g |
| Lauric acid | 3 g |
| Sodium hydroxide | 3.8 g |
| Glycerine | 22 g |
| Propylene glycol | 22 g |
| 1,2-Dodecanediol | 7 g |
| Tetrasodium ethylenediaminetetraacetate | 0.2 g |
| Tetrasodium 1-hyroxyethylidene-diphosphonate | 0.1 g |
| Colorant, perfume | q.s. |
| Water | q.s. 100 g |

EXAMPLE 2

A transparent, solid soap of the following composition is prepared:

| | |
|---|---|
| Stearic acid | 24.2 g |
| Lauric acid | 3.3 g |
| Sodium hydroxide | 4.2 g |
| Glycerine | 25 g |
| Propylene glycol | 25 g |
| 1,2-Dodecanediol | 5.5 g |
| Tetrasodium ethylenediaminetetraacetate | 0.2 g |
| Tetrasodium 1-hydroxyethylidene-diphosphonate | 0.1 g |
| Colorant, perfume | q.s. |
| Water | q.s. 100 g |

EXAMPLE 3

A transparent, solid soap of the following composition is prepared:

| | |
|---|---|
| Stearic acid | 22 g |
| Lauric acid | 3 g |
| Sodium hydroxide | 3.8 g |
| Glycerine | 24 g |
| Propylene glycol | 20 g |
| 1,2-Dodecanediol | 6 g |
| Sodium ($C_{14}$-$C_{16}$)-olefinsulphonate sold at a concentration of 37% of active substance (AS) under the name "Elfan OS46" by Akzo | 4 g AS |
| Tetrasodium ethylenediaminetetraacetate | 0.2 g |
| Tetrasodium 1-hydroxyethylidene-diphosphonate | 0.1 g |
| Colorant, perfume | q.s. |
| Water | q.s. 100 g |

EXAMPLE 4

A transparent, solid soap of the following composition is prepared:

| | |
|---|---|
| Stearic acid | 22.5 g |
| Lauric acid | 3.5 g |
| Sodium hydroxide | 4.0 g |
| Glycerine | 19 g |
| Propylene glycol | 21 g |
| 1,2-Dodecanediol | 7 g |
| Potassium salt of the condensate of copra fatty acids with a hydrolysed animal protein sold at a concentration of 30% AS under the name "Lamepon S" by Grunau | 6 g AS |
| Tetrasodium ethylenediaminetetraacetate | 0.2 g |
| Tetrasodium 1-hydroxyethylidene-diphosphonate | 0.1 g |
| Colorant, perfume | q.s. |
| Water | q.s. 100 g |

EXAMPLE 5

A transparent, solid soap of the following composition is prepared:

| | |
|---|---|
| Stearic acid | 22 g |
| Lauric acid | 3 g |
| Sodium hydroxide | 3.8 g |
| Glycerine | 22 g |
| Propylene glycol | 22 g |
| 1,2-Dodecanediol | 6 g |
| Ether of glucose and of decyl alcohol sold at a concentration of 50% of active substance (AS) under the name "Triton CG 312" by Seppic | 6.4 g AS |
| Tetrasodium ethylenediaminetetraacetate | 0.2 g |
| Tetrasodium 1-hydroxyethylidene-diphosphonate | 0.1 g |
| Colorant, perfume | q.s. |
| Water | q.s. 100 g |

EXAMPLE 6

A transparent, solid soap is obtained by replacing the 6 g of 1,2-dodecanediol in Example 3 with 6 g of 1,2-tetradecanediol.

EXAMPLE 7

A transparent, solid soap is obtained by replacing the 6 g of 1,2-dodecanediol in Example 3 with 6 g of 1,2-decanediol.

EXAMPLE 8

A transparent, solid soap is obtained by reproducing Example 3, with replacement of the 4 g of Elfan OS46 with 6 g (AS) of a sodium (linear $C_{12}$-$C_{14}$)-alkyl ether sulphate containing 2.2 moles of ethylene oxide, sold at a concentration of 70% of active substance (AS).

EXAMPLE 9

A transparent, solid soap of the following composition is prepared:

| | |
|---|---|
| Stearic acid | 19.85 g |

-continued

| | |
|---|---|
| Lauric acid | 3.50 g |
| Sodium hydroxide | 3.75 g |
| Glycerine | 8 g |
| Sorbitol at a concentration of 70% (AS) in aqueous solution | 9 g AS |
| Propylene glycol | 20 g |
| 1,2-Dodecanediol | 6 g |
| Sodium (branched $C_{13}$–$C_{15}$)-alkyl ether sulphate containing 3 moles of ethylene oxide, sold under the name "Tensagex DLM 970" by ICI | 6 g AS |
| Tetrasodium ethylenediaminetetraacetate | 0.2 g |
| Tetrasodium 1-hydroxyethylene-diphosphonate | 0.1 g |
| Colorant, perfume | q.s. |
| Water | q.s. 100 g |

We claim:

1. Composition in the form of a transparent, solid cake, which contains a soap consisting of salts of $C_{10}$–$C_{20}$ fatty acids, a 1,2-alkanediol containing from 10 to 14 carbon atoms, a transparency agent and water in quantities of less than or equal to 25% relative to the total weight of the composition.

2. Composition according to claim 1, wherein the 1,2-alkanediol is 1,2-dodecanediol.

3. Composition according to claim 1, wherein the 1,2-alkanediol is present in proportions between 3 and 10% relative to the total weight of the composition.

4. Composition according to claim 1, wherein the soap consists of sodium salts of $C_{16}$–$C_{20}$ fatty acids or sodium salts of $C_{10}$–$C_{14}$ fatty acids or mixtures thereof.

5. Composition according to claim 1, wherein the soap is present in proportions of between 25 and 40% by weight relative to the total weight of the composition.

6. Composition according to claim 4, wherein the soap consists of 80 to 90% of sodium salts of $C_{16}$–$C_{20}$ fatty acids and of 10 to 20% of sodium salts of $C_{10}$–$C_{14}$ fatty acids by weight relative to the whole quantity of soap.

7. Composition according to claim 1, wherein the transparency agents are chosen from $C_2$–$C_6$ polyols, urea and mixtures of these.

8. Composition according to claim 7, wherein the polyol is glycerine, propylene glycol or sorbitol or mixtures of these.

9. Composition according to claim 1, wherein the transparency agent is present in proportions of 25 to 50% by weight relative to the total weight of the composition.

10. Composition according to claim 1, which contains:
    (i) 25 to 40% of a soap consisting of a mixture of sodium salts of $C_{16}$–$C_{20}$ fatty acids and of sodium salts of $C_{10}$–$C_{14}$ fatty acids;
    (ii) 3 to 10% of 1,2-dodecanediol;
    (iii) 25 to 50% of a $C_2$–$C_6$ polyol or of urea;
    (iv) water in proportions of less than or equal to 25% by weight.

11. Composition according to claim 1, which additionally contains a synthetic anionic or nonionic surface-active agent in proportions of between 1 and 10% relative to the total weight of the composition.

12. Composition according to claim 11, wherein the surface-active agent is chosen from sodium ($C_{14}$–$C_{16}$)-olefin-sulphonates, triethanolamine lauryl-sulphate, sodium N-lauroylsarcosinate, a potassium salt of a condensate of copra fatty acids and of a hydrolysed protein, an ether of glucose and of decyl alcohol, or a sodium (linear or branched $C_9$–$C_{18}$)-alkyl ether sulphate containing 1 to 10 moles of ethylene oxide.

13. Composition according to claim 1, which contains sequestering agents.

14. Composition according to claim 1, which contains adjuvants chosen from pearlescent agents and nonvolatile silicones, skin conditioning agents, extracts of aloe or of mallow, sunflower oil, collagen or colorants.

15. Process of washing the skin, wherein a cosmetic composition in the form of a transparent, solid cake such as claimed in claim 1 is applied to moist skin.

* * * * *